(12) United States Patent
Bellinger et al.

(10) Patent No.: US 12,055,532 B2
(45) Date of Patent: Aug. 6, 2024

(54) SYSTEMS AND METHODS FOR VAPORIZER ANALYSIS

(71) Applicant: EVOLV, LLC, Ashtabula, OH (US)

(72) Inventors: James Bellinger, Akron, OH (US); John Bellinger Decker, Pittsburgh, PA (US)

(73) Assignee: EVOLV, LLC, Hudson, OH (US)

( * ) Notice: Subject to any disclaimer, the term of this patent is extended or adjusted under 35 U.S.C. 154(b) by 0 days.

(21) Appl. No.: 16/382,564

(22) Filed: Apr. 12, 2019

(65) Prior Publication Data
US 2019/0313697 A1 Oct. 17, 2019

Related U.S. Application Data

(60) Provisional application No. 62/656,921, filed on Apr. 12, 2018.

(51) Int. Cl.
| | | |
|---|---|---|
| *G01N 33/00* | (2006.01) | |
| *A24F 15/01* | (2020.01) | |
| *A24F 40/00* | (2020.01) | |
| *A24F 40/51* | (2020.01) | |
| *A24F 40/65* | (2020.01) | |
| *H05B 3/46* | (2006.01) | |
| *A24F 40/10* | (2020.01) | |

(52) U.S. Cl.
CPC .......... *G01N 33/0011* (2013.01); *A24F 15/01* (2020.01); *A24F 40/00* (2020.01); *A24F 40/51* (2020.01); *A24F 40/65* (2020.01); *H05B 3/46* (2013.01); *A24F 40/10* (2020.01)

(58) Field of Classification Search
CPC . G01N 33/0011; G01N 33/0075; A24F 15/01; A24F 40/00; A24F 40/51; A24F 40/65; A24F 40/10; H05B 3/46; H05B 1/0227; H05B 3/16
See application file for complete search history.

(56) References Cited

U.S. PATENT DOCUMENTS

| | | | | |
|---|---|---|---|---|
| 2014/0300480 A1* | 10/2014 | Xiang | ..................... | A24F 40/80 356/439 |
| 2019/0098934 A1* | 4/2019 | Szabo | ........................ | A24F 7/00 |
| 2019/0295304 A1* | 9/2019 | Janardhan | ............. | G06T 13/205 |
| 2021/0037891 A1* | 2/2021 | Fard | ........................ | A24F 40/53 |
| 2021/0044689 A1* | 2/2021 | Fard | ........................ | A24F 40/65 |

* cited by examiner

*Primary Examiner* — Xin Y Zhong
(74) *Attorney, Agent, or Firm* — Tucker Ellis LLP

(57) ABSTRACT

Provided are a system and method of reproducing individual puffs based on empirical data collected by a plurality of electronic vaping devices during use of the vaping devices by users to inhale vapors. The method involves receiving, over a communication network for each of the plurality of electronic vaping devices: (i) reservoir information indicative of a configuration of a reservoir storing a liquid that is at least partially converted into the vapor, and (ii) a plurality of operational parameters for each of a plurality of puffs drawn by the users. The operational parameters include a first operational parameter measured by a sensor system provided to the respective electronic vaping device. An evaluation vaping device is controlled to reproduce a puff by generating a vapor based on the received reservoir information and the received plurality of operational parameters in effect during the puff that is being reproduced.

7 Claims, 4 Drawing Sheets

SYSTEMS AND METHODS FOR VAPORIZER ANALYSIS

BACKGROUND OF THE INVENTION

1. Field of the Invention

This application relates generally to apparatuses and methods for accurately modeling a vapor generated under actual usage conditions and, more specifically, for recording and acquiring parameters of an electronic vaping device used by consumers to accurately reproduce the vapor in an analytical setting.

2. Description of Related Art

Products such as cigarettes that generate smoke to be inhaled are tested to identify and quantify the chemical constituents of the smoke that smokers are exposed to. The tests for chemical constituents may be performed in accordance with standards enacted by a standard-setting body, such as the International Organization for Standardization for example, so different cigarettes can be subjected to an apples-to-apples comparisons to each other. Such comparisons are useful in providing an indication of the level of chemical constituents in the smoke from each cigarette relative to the smoke from other cigarettes. However, the test results obtained under standardized conditions for such relative comparisons do not realistically represent the level of chemical constituents in the actual cigarette smoke inhaled by smokers.

For example, cigarette smokers may opt for so-called "light" cigarettes in an attempt to limit their exposure to certain chemical constituents found in cigarette smoke. Light cigarettes may include structural features such as vent holes formed in the paper wrapper cylindrically encapsulating the tobacco and filter. The vent holes are intended to introduce air through the wrapper into the smoke being inhaled, thereby diluting the quantities of tar, nicotine, carbon monoxide, etc. inhaled by smokers. Standardized test procedures may require a test puff of smoke lasting exactly one second in duration to be drawn by a test device from the light cigarette once every minute. As a result, a substantial portion of a light cigarette being tested burns away between test puffs, falsely limiting the amount of smoke drawn during the test procedure. Test devices compliant with the standardized test procedure are also designed to avoid covering or otherwise blocking the vent holes. The smoke drawn during each test puff is then tested to measure the chemical constituents present.

However, human smokers will often intentionally or inadvertently cover the vent holes with their fingers or lips while smoking cigarettes, thereby blocking the introduction of air during puffs and defeating the intended purpose of the vent holes. Further, smokers who may have a limited amount of time to smoke a cigarette during a work break or in a designated smoking area, for example, will take puffs more frequently than once every minute, and such puffs will often last longer than one second. As a result, the smoke from a light cigarette actually inhaled by smokers will be less diluted with air than the smoke drawn by the test device according to the standardized test procedure. Smokers will actually inhale a much larger quantity of the more-concentrated smoke from a light cigarette than the test devices operating in compliance with the standardized test procedure. The differences between actual smoking habits and the standardized test procedures cause the standardized test procedures to drastically misrepresent the chemical constituents that smokers actually inhale.

More recently, vaping devices have been developed as a substitute for smoking traditional tobacco cigarettes. Vaping devices include a heat source and a reservoir storing what is referred to as an "e-liquid" or "juice." The e-liquid is heated by a heating element to form a vapor of the e-liquid, which is then inhaled by a user. Standardized test procedures have also been developed in an effort to determine what chemical constituents are inhaled by people using a vaping device. However, vaping devices offer users a wide variety of controls, meaning that there are an even-greater number of variables controlled by users of vaping devices than the number of variables controlled by cigarette smokers. Further, some vaping devices are configurable by users to utilize various structures such as different e-liquids, different reservoir structures, etc., or operate at different power levels. Any standardized test procedure developed for vaping devices will likely not take into consideration differences in user-specific control settings and configurations that are likely to have a substantial impact on the results of such standardized test procedures. Consequently, the results of such standardized tests will not accurately represent the chemical constituents actually inhaled by users of vaping devices.

BRIEF SUMMARY OF THE INVENTION

According to one aspect, the subject application involves an electronic vaping device that includes a heating element configured to elevate a temperature of a liquid and convert a portion of the liquid into a vapor to be inhaled by a user of the electronic vaping device. A controller controls delivery of electric energy from a power source to the heating element according to an input from the user, and a sensor system measures at least a first operational parameter of the heating element during operation of the heating element. A computer-readable medium provided in local communication with the controller stores: (i) reservoir information indicative of a configuration of a reservoir storing the liquid, and (ii) a plurality of operational parameters of the electronic vaping device for each of a plurality of puffs. The operational parameters includes at least the first operational parameter. A communication interface in communication with the computer-readable medium transmits the reservoir information and the plurality of operational parameters of the electronic vaping device for the plurality of puffs to a remote computer terminal.

According to an embodiment, the electronic vaping device can further include a reservoir that stores the liquid, wherein the heating element is enclosed by a portion of the reservoir and is separable from the controller as a portion of the reservoir.

According to an embodiment, the electronic vaping device can further include a wicking material that transports the portion of the fluid stored by the reservoir to the heating element.

According to an embodiment, the sensor system includes a temperature sensor that measures a temperature of the heating element as the first operational parameter.

According to an embodiment, a temperature of the heating element is determined as a function of the measured resistance of the heating element during operation.

According to an embodiment, the determined temperature is a peak temperature of the heating element reached during each of the plurality of puffs.

According to an embodiment, the temperature measured by the temperature sensor is a peak temperature of the heating element reached during each of the plurality of puffs.

According to an embodiment, the plurality of operational parameters further include a value indicative of electric power supplied to the heating element for each of the plurality of puffs.

According to an embodiment, the sensor system further includes an airflow sensor that measures a property of an airflow drawn over the heating element during each of the plurality of puffs.

According to an embodiment, the temperature sensor measures a temperature of the heating element as a function of a sensed resistance of the heating element during operation.

According to an embodiment, the operational parameters stored by the computer-readable medium includes a time associated with each of the plurality of puffs.

According to an embodiment, the time includes at least one of: a start time, and end time, and a duration of each of the plurality of puffs.

According to an embodiment, the sensor system includes a power sensor that measures electric power supplied to the heating element as the first operational parameter for each of the plurality of puffs.

According to an embodiment, the power sensor is integrated as a portion of the controller.

According to an embodiment, the sensor system includes an airflow sensor that measures a property of an airflow drawn over the heating element during each of the plurality of puffs.

According to another aspect, the subject application involves a method of reproducing puffs based on empirical data collected by a plurality of electronic vaping devices during use of the vaping devices by users to inhale vapors. The method includes receiving, over a communication network for each of the plurality of electronic vaping devices: (i) reservoir information indicative of a configuration of a reservoir storing a liquid that is at least partially converted into the vapor, and (ii) a plurality of operational parameters for each of a plurality of puffs drawn by the users. The operational parameters include at least a first operational parameter measured by a sensor system provided to the respective electronic vaping device. The method also includes controlling operation of an evaluation vaping device to generate a vapor that is representative of vapors generated during the plurality of puffs. The vapor is generated based on the received reservoir information and the received plurality of operational parameters.

According to an embodiment of the method, controlling operation of the evaluation vaping device includes controlling operation of a heating element of the evaluation vaping device to convert at least a portion of the liquid supplied by a reservoir identified by the received reservoir information.

According to an embodiment of the method, controlling operation of the evaluation vaping device comprises establishing a plurality of operational settings of the evaluation vaping device based on the received plurality of operational parameters.

According to an embodiment of the method, at least one of the operational settings of the evaluation vaping device is established based on an average value of one of the received plurality of operational parameters.

According to an embodiment of the method, at least one of the operational settings of the evaluation vaping device is established based on a peak value of one of the received plurality of operational parameters.

According to an embodiment, the method further includes causing introduction of the vapor generated by the evaluation vaping device to an analytical system to determine a quantity of at least one chemical constituent of the vapor.

According to an embodiment of the method, each of a plurality of the reproduced vapors is generated based on the reservoir information, and the plurality of operational parameters corresponding to one of the puffs generated by a specific vaping device, reproducing the puffs under the actual operating conditions.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF SEVERAL VIEWS OF THE DRAWING

The invention may take physical form in certain parts and arrangement of parts, embodiments of which will be described in detail in this specification and illustrated in the accompanying drawings which form a part hereof and wherein.

DETAILED DESCRIPTION OF THE INVENTION

Figure 1:
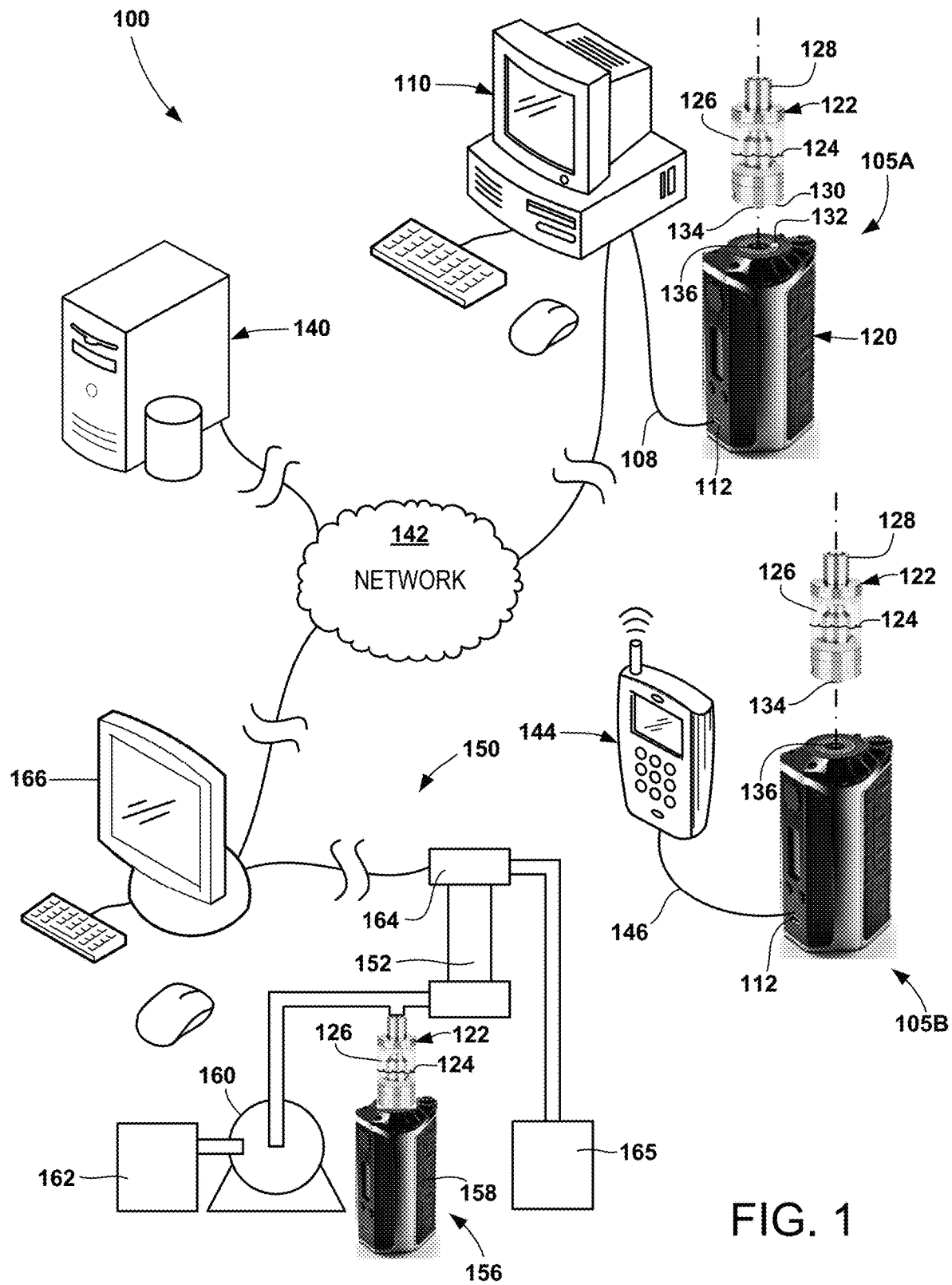
FIG. 1 shows an illustrative embodiment of a network environment for communicating reservoir information and operational parameters of vaping devices used by different users to a recipient for evaluating puffs based on empirical data.

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

Accordingly, there is a need in the art for an apparatus, system and method to identify chemical constituents of a vapor generated by a vaping device under actual usage conditions by users. Such an apparatus, system and method can account for user-specific control and/or configuration preferences of the vaping device while the vaping device is in actual use by users who inhale the vapor.

Generally, a user of the inventive electronic vaping device places an end of a mouthpiece in their mouth and selectively activates a heating element to convert a portion of the e-liquid stored in a reservoir of an atomizer into a vapor. As the user inhales through their mouth, ambient air is drawn into the atomizer and the vapor generated by the heating element is inhaled into the user's lungs. Each individual process involving activation of the heating element and inhalation of the vapor generated by the activated heating element is referred to herein as a "puff."

Reservoir information indicative of the identity or configuration of the atomizer can be stored in a local computer-readable medium provided to the electronic vaping device, a computer terminal connected to the electronic vaping device, or a combination thereof. The reservoir information can include at least one of: data indicating a capacity of the reservoir, dimensions of the airflow passages of the atomizer, a composition or other properties of the e-liquid stored in the reservoir and converted into a vapor, electrical properties of the atomizer, etc.

A plurality of operational parameters measured by a sensor system provided to the electronic vaping device for each of a plurality of puffs is locally stored in the computer-readable medium provided to the electronic vaping device, optionally in real time, as the puffs occur. For example, the puffs can be stored in the computer-readable medium during the puffs, when the puffs are initiated, after the puffs are complete, or at any other desired time. In other words, the operational parameters of the puffs can be stored at any time when such operational parameters are available. The operational parameters are said to be stored locally in the computer-readable medium because the computer-readable medium forms a component of the electronic vaping device used to generate the vapor. Thus, even in the absence of a connection to a different terminal including a separate computer-readable medium, the operational parameters are stored onboard the electronic vaping device itself until a time when they are exported to a different computer terminal. Examples of the plurality of operational parameters for each of a plurality of puffs locally stored by the computer-readable medium include, but are not limited to, at least two of: a peak temperature reached by the heating during the puff, an average temperature of the heating element during the puff, a temperature profile (e.g., data relating temperature to time during the puff), the resistance of the heating element during the puff, a change in the resistance of the heating element during the puff, data for an electrical resistance profile of the heating element (e.g., a set of data samples collected during a puff and any aggregated data such as a value or average value of the set of data samples), a measure of the power supplied to the heating element during the puff, a volume of air over the heating element during the puff, a velocity of air flowing over the heating element. Other details about each puff, such as start time, puff duration, and/or end time can also be locally stored by portable computer-readable medium in the electronic vaping device.

For electronic vaping devices that lack a native, built-in wide-area-network communication ability (e.g., lack a cellular communication antenna or a subscriber identity module "SIM" card), a communication interface of the electronic vaping device can be locally connected to, and optionally hardwired directly to a computing device having network connectivity. Such a connection tethers the electronic vaping device to the computing device, and allows the operational parameters locally stored by the computer-readable medium of the electronic vaping device to be transmitted over this local connection to the computing device. In turn, the computing device can transmit the operational parameters and the reservoir information over a wide-area communication network such as the Internet, for example, to a database server or other suitable recipient terminal. The transmitted data for each puff can be stored in a database, from where it can be retrieved and used to configure an evaluation vaping device to reproduce a vapor representative of the vapor generated for the various puffs under actual usage conditions. The reproduction vapor can be introduced to an analytical system to identify and/or measure quantities of chemical constituents found within the reproduction vapor. According to the inventive system, apparatus and method, the identity and optionally the quantity of the chemical constituents to which users of the electronic vaping devices are exposed under actual usage conditions can be accurately determined.

With reference to the drawings, FIG. 1 shows an illustrative embodiment of a network environment 100 for measuring and aggregating empirical data with vaping devices 105A, 105B, while the vaping devices 150A, 105B are in use under actual usage conditions for different users. Although two vaping devices 105A, 105B used by end users under actual usage conditions are shown and described for illustrative purposes, the network environment 100 can include any number of vaping devices 105A, 105B. Further, the vaping device will be generically referred to herein as vaping device 105.

The actual usage conditions are those freely specified by users inhaling the vapor, and are independent of any standardized conditions or constraints. For example, the actual usage conditions can involve performing puffs of any desired duration, at any desired frequency or interval, at operating temperatures of the heating elements of the vaping devices 105A, 105B specified by the users, according to their own personal preferences. In other words, users who use the vaping devices 105A, 105B under actual usage conditions are doing so according to their own free will, and are not constrained by operational limitations dictated by a study or other experimental procedure specifically designed to gather data as part of a study. Instead, the actual usage conditions are limited only by the limits imposed by the vaping devices 105A, 105B themselves, and may vary by device. For example, the duration of a puff may be limited to a maximum permissible time (for example, up to 20 seconds) that can be arbitrarily selected by a manufacturer or other party responsible for the design of the vaping devices 105A, 105B. Similarly, a controller 224 described below with reference to FIG. 2 may limit the temperature of the heating element to temperatures less than or equal to a maximum temperature such as 600° F., for example.

Described in greater detail below with reference to FIG. 2, each electronic vaping device 105 includes a vaporizer 120 that is operational to supply electric energy to an atomizer 122 to convert a portion of an e-liquid 124 stored in a reservoir 126 of the atomizer 122 into a vapor. The embodiment of the vaping device 105 in FIG. 1 includes an atomizer 122 that is removable, and capable of being re-installed or replaced by a compatible replacement atomizer. The atomizer 122 includes a first connector 134 (e.g., a male threaded member in FIG. 1) that cooperates with a second connector 136 (e.g., a female threaded receiver in FIG. 1) to install the atomizer 122 on the vaporizer 120 in a removable manner. However, it is to be understood that other embodiments of the vaping device 105 can include a permanent atomizer, that is formed as an integral component of the vaporizer and is not removable from the vaporizer.

The term "vapor," as used herein, refers to the combination of air flowing over the heating element, comprising gaseous molecules of the e-liquid evaporated as a result of being exposed to an elevated temperature of a heating element provided to the vaping device 105, and small liquid droplets of the e-liquid suspended or entrained in the air as an aerosol. It is the vapor that is inhaled by a user of the vaping device 105 through a mouthpiece 128, which is provided to the atomizer 122 in the embodiment appearing in FIG. 1.

The network environment 100 includes a computing device 110 to which one or more of the vaping devices 105A, 105B can be tethered by a direct communication channel 108 such as a hard-wired USB cable, or a short-range local-area wireless connection, for example. The direct communication channel 108 can be a peer-to-peer connection extending between an input/output port (e.g., USB port, Bluetooth antenna, etc.) provided to the computing device 110 and a compatible communication interface 112 provided to the vaping device 105A, described below. The computing device 110 can include a non-transitory computer-readable medium storing instructions for an application that, when executed by a processor provided to the computing device 110, establishes communications between the computing device 110 and the vaping device 105A via the communication channel 108. According to alternate embodiments, the computer-executable instructions can optionally be stored by a computer-readable medium 202 (FIG. 2) or other storage device provided to the vaping device 105A, to be executed by the computing device 110 when tethered to the vaping device 105A. As part of such communications, the vaping device 105A can transmit a plurality of operational parameters stored by the non-transitory computer readable medium 202 provided onboard the vaping device 105A to the computing device 110.

In addition to the operational parameters, the computer readable medium 202 provided to the vaping device 105 can also optionally store reservoir information. The reservoir information is indicative of a configuration of the reservoir 126 of the atomizer 122 storing the e-liquid 124, or another portion of the atomizer 122. For example, once an atomizer 122 has been installed on the vaporizer 120, and optionally in response to installation of the atomizer 122, the controller 224 (FIG. 2) can initiate a process of interrogating the heating element to determine a baseline resistance of the heating element, at a time when the atomizer 122 is installed. According to alternate embodiments, the resistance of the heating element can be measured in response to selection of a fire button 226 (FIG. 2) as described below, or in response to any other trigger of a puff. As another example, for embodiments of the vaping device 105 that include a removable atomizer 122 as shown in FIG. 1, the atomizer 122 can optionally include a code, structure or other marking that identifies the atomizer 122, and optionally the e-liquid 124 therein. By way of example, a lower surface 130 of the atomizer 122 can bear a marking such as a barcode or other computer-readable code that can be interrogated by a code reader 132 provided to the vaporizer 120. The code reader 132 can be an optical barcode scanner, or other suitable device positioned on the vaporizer 120 to read the barcode or other marking or identification structure as the atomizer 122 is installed. According to other embodiments, the first connector 134 that couples the atomizer 122 to the vaporizer 120 can be configured with a structure that, when the atomizer 122 is installed on the vaporizer 120, identifies the atomizer 122 and/or e-liquid. The reservoir information stored by the computer readable medium 202 provided to the vaping device 105 can also be transmitted to the tethered computing device 110 via the communication channel 108.

According to alternate embodiments, however, the application executed by the computing device 110 can be utilized by the user to specify the reservoir information such as the identity of the atomizer 122 and/or the e-liquid 124 stored by the reservoir 126. For such embodiments, the reservoir information stored by the computing device 110 can be associated with the operational parameters received by the computing device 110 from the vaping device 105A via the communication channel 108.

Regardless of the information received by the computing device 110, since the vaping device 105A lacks a native wide-area-network communication capability, the network communication resources of the computing device 110 can be leveraged to transmit the received information to a remote server 140. The computing device 110 can be a home computer or otherwise associated with a user of the vaping device 105A, and the server 140 can be remotely located at a different location, but accessible by the computing device 110 over a wide-area-network 142 such as the Internet, for example. The server 140 can be operated by, or on behalf of a manufacturer associated with the vaping device 105A, or otherwise be accessible to be used for configuring an evaluation vaping device of a test system to reproduce the puffs under conditions based on the received information.

According to an alternate embodiment, the vaping device 105B can be tethered to a different computing device 110, or a terminal other than the computing device 110. As shown in FIG. 1, the vaping device 105B is tethered to a cellular telephone 144. The cellular telephone 144 includes a SIM card, affording it a wide-area-network communication ability. Similar to the vaping device 105A transmitting the operational parameters and optionally reservoir information to the computing device 110, the vaping device 150B can transmit the operational parameters and optionally reservoir information to the cellular terminal via the communication channel 146. In turn, the cellular telephone 144 can transmit the received operational parameters and optional reservoir information over a wide area network 142 such as a cellular communication network and/or the Internet, to be received and stored by the server 140. Similar to the communication channel 108, the communication channel 146 can be a direct, wired or wireless connection established by a USB cable, short-range wireless protocol, etc. extending between a communication interface 112 provided to the vaping device 105B and a compatible communication port provided to the cellular telephone 144.

The server 140 or other remote terminal can be utilized to aggregate the received data in a database. The operational parameters for each puff are stored in association with the reservoir information and any other information (e.g., a serial number) identifying each of the different puffs for which information is received over the communication network 142. The data can optionally be grouped according to the atomizer 122 or properties thereof, the e-liquid, or according to any other categorization scheme. The stored data can be sortable or filterable within the database to allow for retrieval and use of the stored data to reproduce the puffs under the actual usage conditions for which the stored data was recorded. Such an analysis can optionally involve the performance of a qualitative and/or quantitative analysis of the chemical composition of the vapor produced by each puff. For example, the network environment 100 can also include an analytic system 150 that can be configured based on the empirically-collected data stored in the database for a specific atomizer 122 to accurately reproduce a vapor for puffs performed under actual usage conditions. The reproduction vapor representing the puffs can be introduced to the analytic system 150 which, in turn, subjects the vapor to one or more tests to determine the actual chemical constituents, and optionally their quantities, to which users are actually exposed.

For the embodiment in FIG. 1, the analytic system 150 includes a high performance liquid chromatography ("HPLC") column 152. An evaluation vaping device 156 can be configured to include the same, or a structurally comparable atomizer 122 used by the vaping devices 105A, 105B. The vaporizer 158 of the evaluation vaping device 156 can be configured with operational parameters based on the received operational parameters transmitted by the vaping devices 105A, 105B. For example, two or more of the operational settings (e.g., a peak temperature, the power supplied to the heating element, the duration of puffs, etc.) of the evaluation vaping device 156 can be established based on an average of the values for such parameters measured during the puffs recorded and transmitted by the vaping devices 105A, 105B.

A pump 160 draws a solvent from a reservoir 162 and elevates the pressure of the solvent to high pressures above 40 atmospheres, for example. The vapor generated for each puff reproduced using the evaluation vaping device 156 is transported by the pressurized solvent into the HPLC column 152. A detector 164 measures the retention time of the vapor in the HPLC column 152, before the waste is expelled into a waste container 165. The retention time is measured from a time at which the vapor is injected into the column to a time when a maximum peak height is reached by each constituent in the vapor is reached within the HPLC column 152. The detector 164 transmits signals indicative of the retention times for the different chemical constituents, and a plot comprising peaks for the different constituents detect is generated by a computing device 166 in communication with the detector 164. Although the above example utilizes HPLC, any desired analysis technique can be used without departing from the scope of the present invention.

Figure 2:
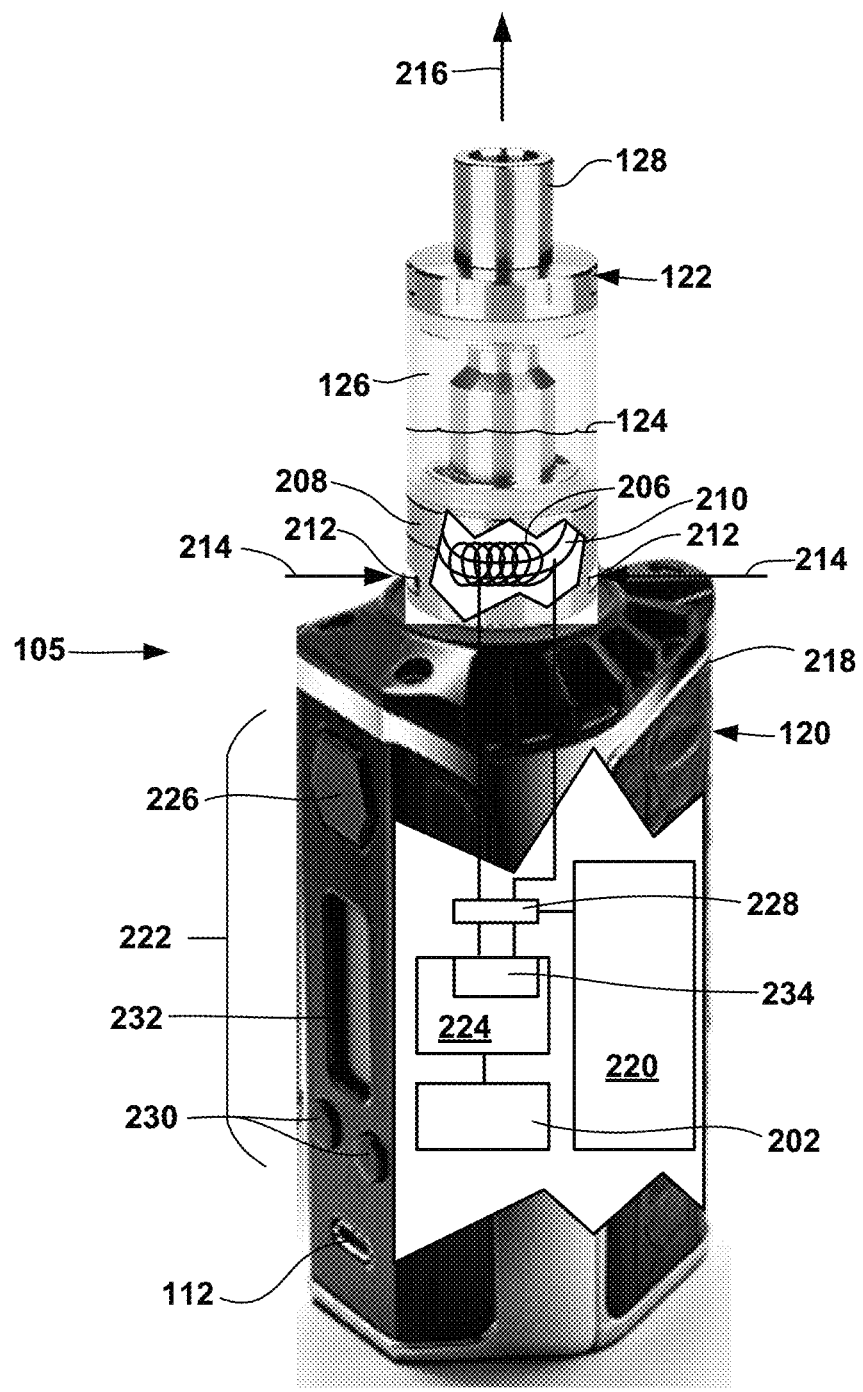
FIG. 2 shows a partially-cutaway embodiment of a vaping device that collects empirical data for actual puffs drawn by a user and transmits the empirical data to be delivered to a recipient over a communication network.

A partially-cutaway view of an illustrative embodiment of the vaping device 105 is shown in FIG. 2. According to the illustrated embodiment, the vaping device 105 includes a heating element 206 enclosed within a housing 208 of the atomizer 122. The illustrated embodiment of the heating element 206 is formed into a coil that encircles a wicking material 210. The wicking material 210 is in fluid communication with the e-fluid 124 in the reservoir 126 defined by the atomizer 122 to convey at least a portion of the e-fluid 124 to the heating element 206 to be converted into the vapor. Alternate embodiments of the atomizer 122 can lack the wicking material 210, including one or more channels through which the e-liquid 124 can be delivered to the heating element 206 from the reservoir. Ambient air is drawn into the interior of the atomizer 122 through one or more vents 212 in the directions indicated generally by arrows 214. The heating element 206 is activated to heat a portion of the e-liquid 124 delivered to the heating element 206 to its boiling point, thereby converting at least a portion of the e-liquid 124 into the vapor that is inhaled through the mouthpiece 128 in the direction indicated generally by the arrow 216.

The vaporizer 120 includes a housing 218 that encloses a power supply 220 such as a battery or battery bank that stores the electric energy used to energize the heating element 206. A user interface 222 can be exposed at a surface of the vaporizer 120 to allow the user to input one or more operational parameters to be established by a controller 224 to generate the vapor during each puff. Examples of the controls provided to the user interface include, but are not limited to, a fire button 226 that, when pressed, causes the controller 224 to close a switch 228 or otherwise electrically connect the power supply 220 to the heating element 206, thereby energizing the heating element 206 to generate the vapor for the puff. According to alternate embodiments, the fire button 226 can be replaced by a control routine programmed into the controller 224 that automatically activates the heating element 206 in response to detecting a negative pressure or the flow of air through the atomizer 122 caused by the user. One or a plurality of power selectors 230 such as tactile or membrane buttons, for example, allow the user to adjust the electric power desired by the user to be delivered to the heating element up and down to a target value. A display device 232 such as a color LCD display, for example, can be provided to convey information concerning the operation of the vaping device 105 to the user. Although an example of the user interface 122 is described above, the user interface 122 could allow for minimal user input, and include simply a notification device such as an LED. For alternate embodiments, a user interface 122 that receives user input can be omitted entirely, the vaping device 105 instead operating according to the control routine that activates the heating element 206 in response to detecting the negative pressure.

A sensor system 234 is provided to the atomizer 122, the vaporizer 120, or both, to measure values of certain operational parameters, as actually implemented during puffs performed using the vaping device 105. For example, the sensor system 234 may include a resistivity sensor integrally formed as part of the controller 224 that measures the resistance of the heating element 206 during a puff. The resistance of the heating element 206 varies as the temperature of the heating element 206 changes. Accordingly, the sensor system 234 can measure changes in the resistivity of the heating element 234 during each puff, which can be correlated to a temperature profile of the heating element 206. For example, the measured resistance of the heating element 206 can be compared to a reference resistance at a known temperature by the controller 224, a processor provided to the computing device 110 or the server 104, or any other terminal for example, to determine to determine a peak temperature, average temperature or other temperature-related value associated with the heating element 206 for that puff.

The sensor system 234 can optionally include a power sensor that measures the electric power supplied to the heating element 206 during each puff. Alternate embodiments can record the user-specified power setting input via the power selectors 230, for example, as the power supplied to the heating element 206 during each puff. The measured power supplied to the heating element 206 can be used with the measured resistance of the heating element 206 to determine a peak temperature, average temperature, or other temperature-related value associated with the heating element 206 for that puff.

The sensor system 234 was described above as being formed as part of the controller, possibly as part of a common circuit board with the controller 224. However, other embodiments of the sensor system 234 can include a discrete sensor separate from the controller 224, provided to the atomizer 122 and operatively connected to the controller 224 as a result of cooperation between the first and second connectors 134, 136 (FIG. 1) connecting the atomizer 122 to the vaporizer 120. For example, a temperature sensor arranged immediately adjacent to the heating element 206 can directly measure the temperature of the heating element 206 during each puff. As another example, an airflow sensor can be disposed within the passages through which the air or the vapor flows during each puff. Such an airflow sensor can measure a volume of air over the heating element 206 during the puff, a velocity of air flowing over the heating element 206 during the puff.

The sensor system 234 can optionally also include a timer that can record temporal information for each puff, such as start time, puff duration, and/or end time. The temporal limitations, and/or the other measured values can be locally stored by portable computer-readable medium 202 in the vaping device 105.

The communication interface 112 of the vaporizer 120 includes a communication port such as a micro-USB, mini-USB, USB-C, Apple Lightning or other suitable wired-connection port used to tether the vaporizer 120 to a computing device 110 or other terminal as shown in FIG. 1. The communication interface 112 can also include a header provided to the controller 224, operatively connecting the communication interface 112 to the computer-readable medium 206 via the controller 224. The operational parameters measured or otherwise recorded in the computer-readable medium 206 for each puff can be transmitted to the tethered computing device 110 or other terminal via the communication interface 112.

Figure 3:
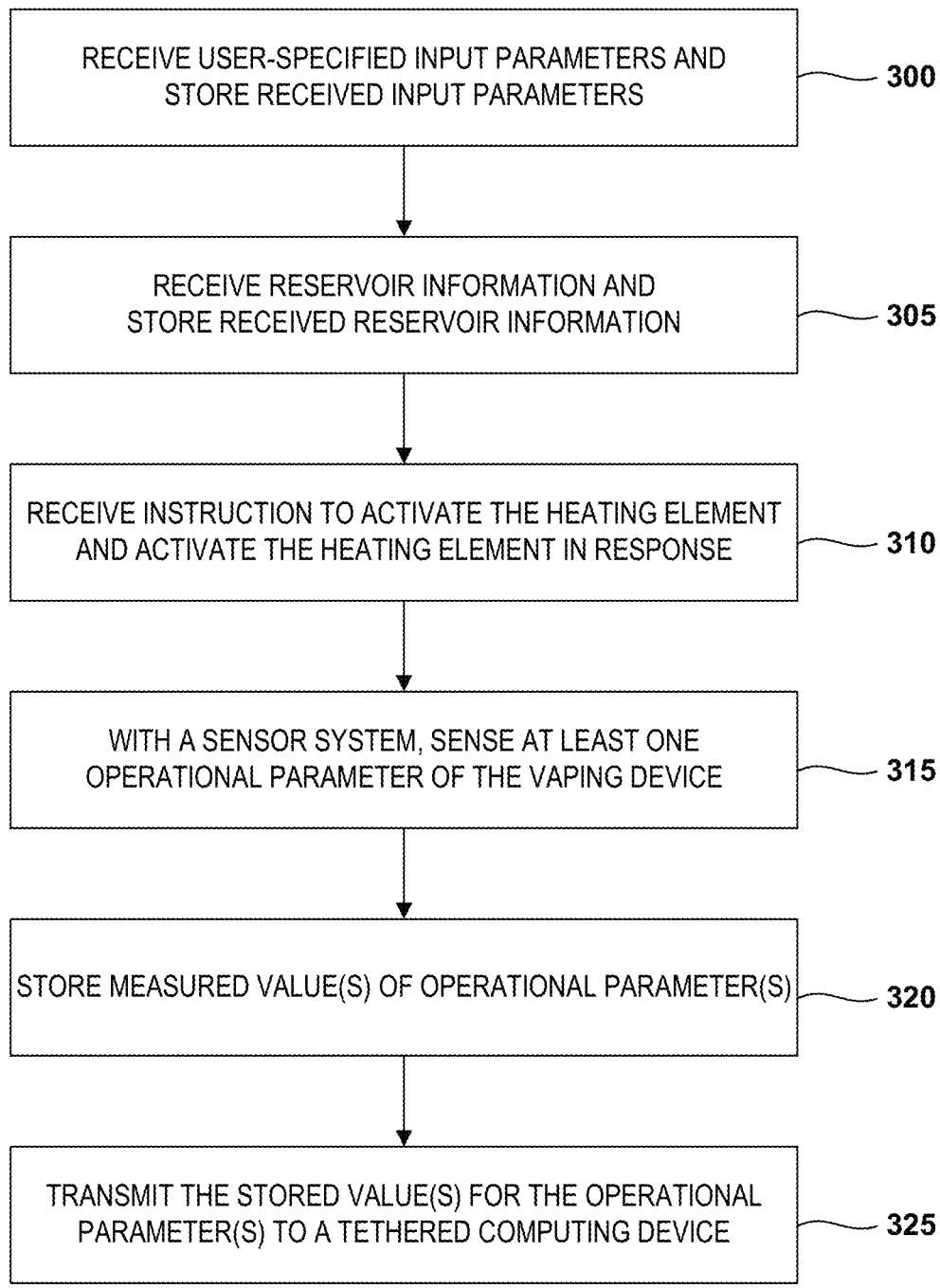
FIG. 3 is a flow diagram schematically depicting an embodiment of a method of collecting and communicating operational parameters for reproduction of puffs under actual usage conditions.

A method of collecting and communicating operational parameters for reproduction of puffs under actual usage conditions is schematically depicted in the flow diagram of FIG. 3. User-specific parameters for puffs that were input via the user interface 222 are received by the controller 224, and stored in the computer-readable medium 224 or other storage device provided to the vaporizer 120 at step 300. One or a plurality of the user-specific parameters can optionally be associated with each puff performed based on such a parameter in the computer-readable medium 206. For embodiments of the vaping device 105 where the atomizer 122 and/or the e-liquid 124 may be changed by the user, reservoir information can optionally be received by the controller 224 and stored in the computer-readable medium 206 at step 305. The reservoir information can be indicative of at least one of: the identity of the atomizer 122, a configuration of the atomizer 122 or reservoir 126, the identity or composition of the e-liquid, electrical properties of the heating element 206 provided to the atomizer 122, and the like.

At step 310, an instruction to energize the heating element 206 for a puff is received by the controller 224. Responsive to receiving such an instruction, the controller causes electric energy to be supplied by the power supply 220 to the heating element 206. The electric energy can be continuously supplied for the duration of the puff as indicated by the pressing of the fire button 226 or the presence of the negative pressure within the atomizer 122, for example. While the heating element 206 is activated ambient air is drawn into the interior of the atomizer 122 through the vent(s) 212 (FIG. 2) and a portion of the e-liquid 124 converted into vapor by the heat is entrained in the airflow and out of the mouthpiece 128.

During the puff, the sensing system 234 measures a value for at least two of the operational parameters at step 315. The values measured by the sensor system 234 is/are locally stored in the computer-readable medium 206, at step 320, until a time when the stored values can be transmitted to a tethered computing device 110 or other terminal. The measure value(s) can be stored in association with the specific puff during which the value(s) was/were measured. For example, each puff can be assigned an identification number. The measured value(s), optionally along with any reservoir information and/or user-specific parameters input via the user interface 222 for puffs, can be associated with the identification number uniquely identifying those puffs in the computer-readable medium 206. Thus, the actual usage conditions for individual puffs can be determined based on the stored information.

Once the communication channel 108 (FIG. 1) has been established between the communication interface 112 and the computing device 110, the controller 224 causes transmission of the information stored in the computer-readable medium 206 to the computing device 110 at step 325. The information is transmitted to maintain the association between the individual puffs and their respective operational parameter values. The computing device 110 can be utilized to transmit the received information over a wide-area-network 142 (FIG. 1) to a database server 140, from where the received information can be retrieved to be analyzed.

Figure 4:
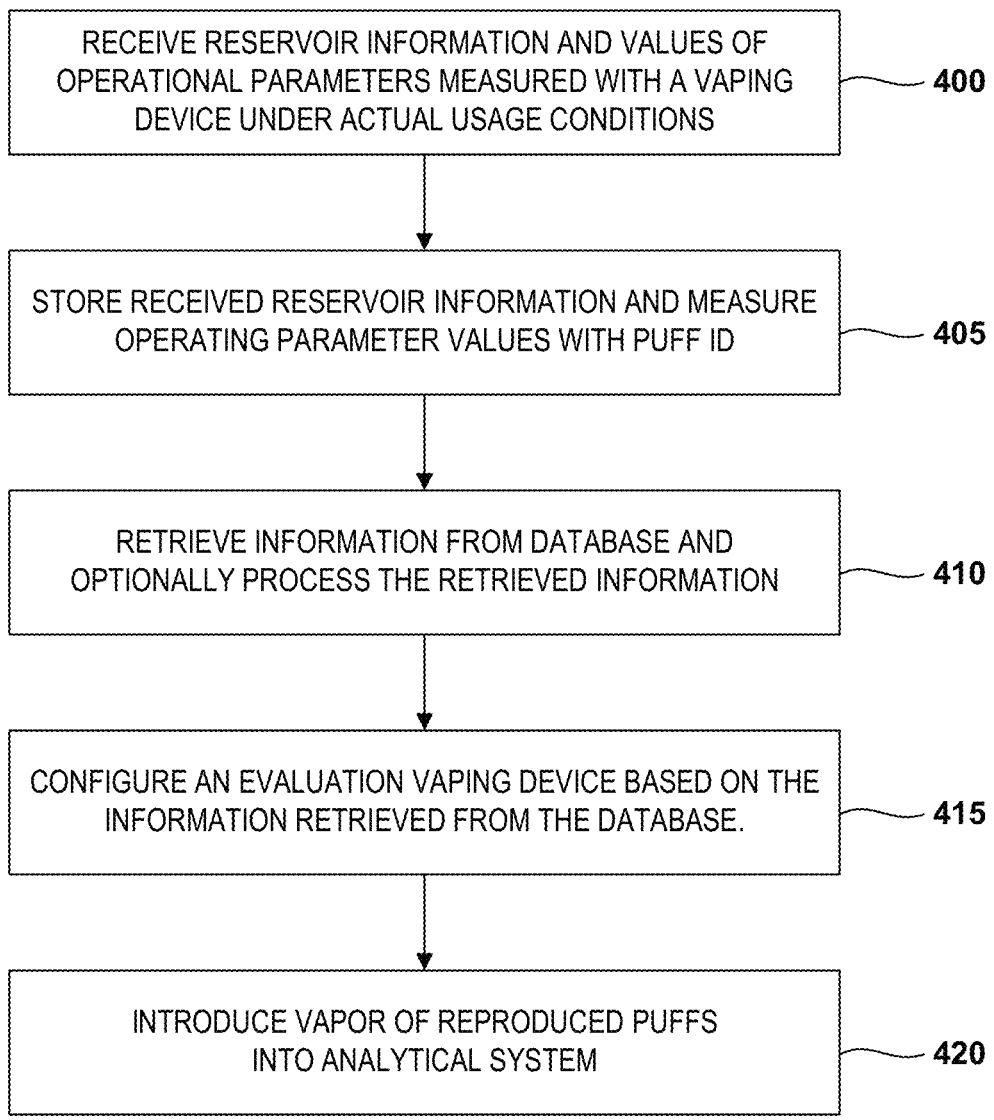
FIG. 4 is a flow diagram schematically depicting an embodiment of a method of measuring operational parameters using a vaping device 105 under actual usage conditions, and reproducing puffs based on the measured operational parameters.

FIG. 4 is a flow diagram schematically illustrating an embodiment of a method of measuring operational parameters using a vaping device 105 under actual usage conditions, and reproducing puffs based on the measured operational parameters. At step 400, the information measured or otherwise obtained and transmitted via the communication interface 112 of the vaping device 105 is received by a server 140 as part of a transmission from the computing device 110 over a wide area network such as the Internet. The received information is stored in a database, at step 405, and associated with the respective puffs during which the received information was measured or otherwise obtained. Thus, the measured values of the operating parameters correspond to their respective puffs in the database.

The information stored in the database in relation to the individual puffs can be retrieved from the database and optionally subjected to pre-reproduction process at step 410. As an example of the pre-reproduction process, the peak temperature measured for each of a plurality of puffs utilizing a specific atomizer 122 can be averaged over a specific time period to determine an average peak temperature of the heating element 206 selected by users. Other examples include determining the average power supplied to the heating element 206, the average airflow over the heating element 206, or the average change in resistance of the heating element 206. The average value of any two operational parameters such as the average peak temperature and the average power delivered, or the average power delivered and the average airflow over the heating element 206, can optionally be determined for purposes of reproducing puffs under comparable operating conditions. Such processed values of the operational parameters can be used in combination with known physical and/or electrical parameters of the atomizer 122 identified by the reservoir information to calculate other parameters to be used to reproduce the puffs for experimental purposes.

At step 415, a controller provided to an evaluation vaping device 158 (FIG. 1) in a lab or other test facility can be programmed based on the data retrieved from the database, optionally as processed at step 410. The data retrieved from the database can be filtered to limit the data used for configuring the evaluation vaping device 158 to information collected using a vaping device 105 that is the same model, optionally with the same atomizer 122, as the evaluation vaping device 158. At step 420, the programmed controller of the evaluation vaping device 158 controls operation of the evaluation vaping device 158 to re-produce the vapor for puffs that were performed under actual usage conditions using the vaping devices 105. The vapor so generated can be introduced to an analytical system 150 (FIG. 1) at step 425 to identify, and optionally quantify at least one chemical constituent in the vapor of the reproduced puffs.

The pre-reproduction process at step 410 is optional to allow. Instead of performing the pre-production process, individual puffs can be reproduced under the actual usage conditions for which the operational parameters were collected. For example, a group (e.g., 200) of users can be selected (randomly, specifically-targeted individuals, individuals within a certain class of users, etc.) from the database. Each of the puffs taken by the selected individuals can be reproduced, on an atomizer of the evaluation vaping device 158 that is equivalent to the atomizer 122 used by those individuals, at the same time intervals during the puffs for which the operational parameters were recorded. For example, for a given configuration, the actual recorded values of temperature and power retrieved from the database can be used to estimate the airflow through the atomizer 122 under the actually usage conditions for each of the puffs. As a result, each individual puff can be reproduced using the evaluation vaping device 154 according to the recorded power and temperature values, along with the estimated air flow. If the measured temperature of the heating element provided to the evaluation vaping device 154 matches the recorded temperature for a puff, within a suitable tolerance, then it is determined that the airflow estimate is essentially correct. Data structures for individual test subjects or a group of subjects can be generated based on the analysis performed using the evaluation vaping device 158 by reproducing puffs performed during a particular report period. For instance, during a given day, user X received 10 milligrams of chemical constituent Y in the vapor, and user Z received a dose of 5 milligrams of W in the vapor. The present systems and methods allow for an accurate determination of the presence of one or more chemical constituents in the vapor generated using specific atomizers, under actual usage conditions, on a large scale. Such a determination can be accomplished optionally without requiring users to deviate from their regular use of the vaping device 105.

The analysis results for puffs reproduced under actual usage conditions can also optionally be combined with survey data collected from users. For example, surveys can be served by the server 140 (or a different network-connected server) over the network environment 100 to the computing device 110. The results of the survey input to the computing device 110 by the user can be stored in the database server 140, and optionally linked to the operational parameters for that user in the database. The surveys can be constructed to elicit detailed information about the user's vaping device 105 such as the specific e-liquid 124 used, the model of the atomizer 122, etc. that may otherwise not be capable of being objectively determined by the controller 224 of the vaping device 105. An incentive can be provided to the users to answer the surveys. For example, users can be offered a discount on the e-fluid as a result of completing the survey. Further, the content of the surveys can optionally be tailored based on the reproduced puff results. For example, users who are determined to receive high doses of nicotine under actual usage conditions may be grouped together as people who are vaping as part of a smoking cessation program. Such users may be asked questions in the survey about smoking cessation options such as e-fluids with relatively high nicotine concentrations, or be asked for opinions about available smoking cessation options. The dissemination of surveys and other such information relevant to individual users, or classes of users, can also be controlled. Referring once again to users who are determined to receive high doses of nicotine under actual usage conditions, email advertisements can be addressed to such users, but not addressed to other users who receive high doses of flavoring as opposed to nicotine, for example.

Illustrative embodiments have been described, hereinabove. It will be apparent to those skilled in the art that the above devices and methods may incorporate changes and modifications without departing from the general scope of this invention. It is intended to include all such modifications and alterations within the scope of the present invention. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A method of reproducing puffs based on empirical data collected by a plurality of electronic vaping devices during use of the vaping devices by users to inhale vapors, the method comprising:
   receiving, over a communication network for each of the plurality of electronic vaping devices: (i) reservoir information indicative of a configuration of a reservoir storing a liquid that is at least partially converted into the vapor, and (ii) a plurality of operational parameters for each of a plurality of puffs drawn by the users, the operational parameters comprising at least a first operational parameter measured by a sensor system provided to the respective electronic vaping device; and
   controlling operation of an evaluation vaping device to generate reproduced vapors that are representative of vapors generated by remotely-located vaping devices during the plurality of puffs under actual operating conditions, wherein the reproduced vapor is generated based on the received reservoir information and the received plurality of operational parameters.

2. The method of claim 1, wherein controlling operation of the evaluation vaping device comprises controlling operation of a heating element of the evaluation vaping device to convert at least a portion of the liquid supplied by a reservoir identified by the received reservoir information.

3. The method of claim 1, wherein controlling operation of the evaluation vaping device comprises establishing a plurality of operational settings of the evaluation vaping device based on the received plurality of operational parameters.

4. The method of claim 3, wherein at least one of the operational settings of the evaluation vaping device is established based on an average value of one of the received plurality of operational parameters.

5. The method of claim 3, wherein at least one of the operational settings of the evaluation vaping device is established based on a peak value of one of the received plurality of operational parameters.

6. The method of claim 1 further comprising causing introduction of the vapor generated by the evaluation vaping device to an analytical system to determine a quantity of at least one chemical constituent of the vapor.

7. The method of claim 1, wherein each of a plurality of the reproduced vapors is generated based on the reservoir information, and the plurality of operational parameters corresponding to one of the puffs generated by a specific vaping device, reproducing the puffs under the actual operating conditions.

* * * * *